United States Patent
Rapp

(10) Patent No.: US 8,876,693 B2
(45) Date of Patent: Nov. 4, 2014

(54) DEVICE AND METHOD FOR VAGINAL SACROCOLPOPEXY

(76) Inventor: David Elliot Rapp, Glen Allen, VA (US)

(*) Notice: Subject to any disclaimer, the term of this patent is extended or adjusted under 35 U.S.C. 154(b) by 729 days.

(21) Appl. No.: 12/924,189

(22) Filed: Sep. 23, 2010

(65) Prior Publication Data

US 2011/0263930 A1    Oct. 27, 2011

Related U.S. Application Data

(60) Provisional application No. 61/342,789, filed on Apr. 21, 2010.

(51) Int. Cl.
| | |
|---|---|
| A61F 2/00 | (2006.01) |
| A61F 13/00 | (2006.01) |
| A61F 2/02 | (2006.01) |
| A61B 17/04 | (2006.01) |
| A61B 17/00 | (2006.01) |

(52) U.S. Cl.
CPC ........... *A61F 2/0045* (2013.01); *A61B 17/0469* (2013.01); *A61B 17/0483* (2013.01); *A61B 2017/0414* (2013.01); *A61B 2017/044* (2013.01); *A61B 2017/00805* (2013.01); *A61B 17/0485* (2013.01)
USPC ............. 600/37; 606/151; 128/897; 128/898; 128/899; 600/29; 600/30

(58) Field of Classification Search
USPC .......... 600/29, 30, 37; 606/151; 128/897–899
See application file for complete search history.

(56) References Cited

U.S. PATENT DOCUMENTS

| | | | |
|---|---|---|---|
| 6,592,515 B2 | 7/2003 | Thierfelder et al. | |
| 7,347,812 B2 | 3/2008 | Mellier | |
| 7,628,155 B2 | 12/2009 | Carey | |
| 7,637,920 B2 | 12/2009 | von Lehe et al. | |
| 2005/0199249 A1 | 9/2005 | Karram | |
| 2007/0161849 A1 | 7/2007 | Goldberg | |
| 2009/0216075 A1* | 8/2009 | Bell et al. ........................ | 600/37 |
| 2010/0197999 A1* | 8/2010 | Deegan et al. .................. | 600/30 |
| 2010/0305394 A1* | 12/2010 | Rosenblatt ...................... | 600/30 |
| 2011/0160527 A1* | 6/2011 | Khamis et al. .................. | 600/37 |
| 2012/0108894 A1* | 5/2012 | Young et al. .................... | 600/37 |
| 2013/0109910 A1* | 5/2013 | Alexander et al. .............. | 600/37 |

* cited by examiner

*Primary Examiner* — Christine Matthews
*Assistant Examiner* — Sunita Reddy

(57) ABSTRACT

A surgical procedure for repairing vaginal prolapse, including apical descent (vaginal vault or uterine descensus), cystocele and/or rectocele, avoids bladder injury, the need for laparoscopic suturing, and difficulties in tensioning the mesh used to hold the vagina in the correct anatomical position, and can be practiced with off the shelf components. The procedure typically comprises exposing a female patient's peritoneum; making a peritoneal incision (e.g. over the patient's sacrum); mobilizing the peritoneum; incising the patient's vagina and attaching the anterior and posterior surfaces of a first (e.g. generally rectangular) mesh component, with a truncated stem and first locking element, to the apex of the patient's vagina; passing a mesh base component having a second locking element at a distal end, and a proximal end, underneath the peritoneum; moving the first and second locking elements together into locking relationship; anchoring the mesh base (e.g. to the sacrum, so that the mesh components suspend the vaginal apex from the sacrum); and closing the peritoneal incision. Particular mesh components with locking elements, and a surgical spreader for use in the procedure, are desirable.

16 Claims, 10 Drawing Sheets

DEVICE AND METHOD FOR VAGINAL SACROCOLPOPEXY

CROSS REFERENCE TO RELATED APPLICATIONS

This application is based upon, and claims the benefit of, U.S. Provisional Application 61/342,789 filed Apr. 21, 2010, the disclosure of which is incorporated by reference herein.

BACKGROUND AND SUMMARY OF THE INVENTION

Every year, thousands of women undergo surgery for vaginal prolapse (falling). Prolapse of the vagina can comprise the descent of multiple surrounding structures, including the bladder, uterus (if no hysterectomy has been performed), vaginal apex (after hysterectomy), and rectum. Vaginal prolapse is the result of weakness of the ligaments and muscles that normally hold the vagina within the pelvis. Vaginal prolapse is associated with multiple risk factors, including child birth, medical disease, obesity, age, and hysterectomy. Vaginal prolapse can result in pain, sexual dysfunction, difficulty in having a bowel movement, urinary incontinence, vaginal ulceration, and/or other problems.

Sacrocolpopexy is presently considered the optimum surgical procedure to correct vaginal vault prolapse. In sacrocolpopexy a generally Y-shaped mesh (as disclosed in U.S. Pat. No. 6,592,515, comprising a pair of angled arms permanently bonded to an elongated stem) is used to hold the vagina in the correct anatomical position. Sacrocolpopexy may be performed as an open surgery by making an approximately 25 cm horizontal incision in the lower abdomen, which allows the surgeon to manually access the inter-abdominal organs. However presently sacrocolpopexy is typically performed laparoscopically, most desirably using robotic assistance.

Irrespective of open or laparoscopic approach, the procedure begins by pushing the vagina back into its natural position using a surgical sizer, which allows for exposure. Then a space is created between the vagina and bladder and also between the vagina and rectum so as to expose the vaginal apex. This is a time consuming part of the procedure and often a source of injury to the bladder. A small incision is then made in the peritoneum to expose the sacrum part of the hip bone. Then the peritoneal incision is opened all the way down to the previously exposed vaginal apex and the mesh inserted. The generally Y-shaped portion of the mesh is sutured to the apex of the vagina while the mesh stem is anchored to the sacrum using suturing or a bone screw, so that the mesh suspends the apex of the vagina from the sacrum. The entire peritoneal incision is then closed using standard suturing.

Other surgical repairs of the vaginal apex may be made using a completely vaginal operation, if the vagina is tacked to a structure other than the sacrum. While this avoids the complications of an abdominal route, in at least one reported study these repairs are associated with inferior results. A completely transvaginal route to the sacrum would be ideal, but is considered by many surgeons to have unacceptable safety issues.

According to the invention, a surgical procedure and device are provided that have many advantages compared to conventional sacrocolpopexy, including removing many of the "danger" or time-consuming steps that presently relegate sacrocolpopexy to experienced lapararoscopic or robotic surgeons.

The device according to the invention comprises a surgical implantable article comprising a two component mesh system with the components connectable together by a locking device, and a surgical spreader assembly. The mesh parts are of biocompatible material and may comprise a first (e.g. generally rectangular) component and a truncated stem, and a separate elongated base component.

In the surgical procedure according to the invention, the generally rectangular mesh component is placed vaginally, and the mesh base abdominally, and they are hooked together with the locking device during the procedure. The mesh base is placed using a unique passing technique that allows the base of the mesh to pass underneath the peritoneum, and avoids having to open up the entire peritoneal incision. After passing, the mesh base is anchored to the sacrum, such as by using conventional suturing or a bone screw and locking ring, other conventional techniques. The abdominal portion of the procedure is most desirably performed laparoscopically. Importantly, there is more than one component to vaginal prolapse [for example both apical descent and a cystocele (bladder drop) and/or rectocele], and according to the invention it is possible to perform a second procedure concurrently to effectively fix the additional defect(s).

More particularly, according to the invention there is provided a surgical implantable article comprising first and second mesh components of biocompatible material. The mesh components may be made of the same material(s) (e.g. biocompatible polypropylene) as the surgical implantable article described in U.S. Pat. No. 6,592,515, the disclosure of which is incorporated by reference herein. The first mesh component may be a generally rectangular component having a truncated stem including a first locking element. The second mesh component comprises an elongated base having distal and proximate ends, with a second locking element operatively associated with the distal end.

As possible modifications of the second mesh component are the following: At the distal end is also a housing unit to allow for stylette insertion. At the proximal end, the elongated base preferably has a thinned neck that allows it to be drawn through a locking ring attached to the sacrum, or a pair of arms, or a wider area, depending upon how the mesh base will be attached to the sacrum.

The first and second locking elements, when moved into operative association with each other, fit together to positively lock the first and second components together, typically for the life of the patient. Any conventional, or hereafter developed, locking element configuration that accomplishes that result is utilizable.

In addition to the surgical implantable article described above, the invention includes several embodiments that facilitate placement and anchoring of the mesh components. One of these includes a surgical spreader assembly comprising spreader jaws connected to a flexible shaft with a removable handle. A sheath is also provided, dimensioned to fit over the flexible shaft and jaws when the handle is removed. Also provided is a stylette which helps advance the mesh base through the sheath (a sheath and stylette per se are shown in U.S. Pat. No. 7,637,920).

Alternatively, the spreader assembly can be replaced with a blunt tip, flexible stylette, and sheath dimensioned to fit over the stylette. In this embodiment standard laparoscopic instruments would be used to mobilize the peritoneum prior to stylette placement.

According to another aspect of the invention there is provided a surgical procedure for repairing female sexual organ problems in a human patient comprising: a) exposing a patient's peritoneum; b) making a peritoneal incision; c) mobilizing the peritoneum; d) attaching a first mesh component with a first locking element to a portion of the patent; e)

passing a second mesh component having a second locking element at a distal end, and a proximal end, underneath the peritoneum; f) moving the first and second locking elements together into locking relationship; g) anchoring the second mesh component to a part of the patient's body so that the mesh components suspend at least a portion of one of the patient's sexual organs; and h) closing the peritoneal incision.

In utilizing the procedure, g) may be practiced to anchor the second mesh component to the sacrum so that the mesh components suspend the vaginal apex from the sacrum; and d) may be practiced by attaching the first mesh component to the apex of the patient's vagina or to the cervix. Also, this surgical procedure may be practiced to repair vaginal prolapse, including apical descent, or vaginal vault or uterine descensus, and/or cystocele and rectocele.

According to another aspect of the invention there is also provided a surgical procedure for repairing vaginal prolapse, including apical descent (vaginal vault or uterine descensus), cystocele and rectocele. According to the procedure of the invention, the following are practiced: a) exposing a patient's peritoneum; b) making a peritoneal incision over the patient's sacrum; c) mobilizing the peritoneum; d) incising the patient's vagina and attaching the anterior and posterior surfaces of a first (e.g. generally rectangular) mesh component, with a truncated stem and first locking element, to the apex of the vagina; e) passing a mesh base component having a second locking element at a distal end, and a proximal end, underneath the peritoneum; f) moving the first and second locking elements together into locking relationship; g) anchoring the mesh base to the sacrum, so that the mesh components suspend the vaginal apex from the sacrum; and h) closing the peritoneal incision.

In the practice of the surgical procedure according to the invention, d) is preferably practiced vaginally, and e) and g) abdominally. Anchoring may be practiced using a variety of conventional techniques, including standard suturing, or using a conventional bone screw affixed to the sacrum and a locking ring affixed to the bone screw, and the mesh base is tensioned using the locking ring and then fixed to the locking ring. Also, c) may be practiced using standard lap equipment, or by passing a spreader, having jaws connected to a flexible shaft underneath the peritoneum, the spreader also having a removable handle, and e) may be practiced by removing the handle of the spreader, passing a sheath over the spreader shaft and jaws to the approximate location of the first locking element, removing the spreader shaft and jaws through the sheath, and using a stylette inserting the base mesh through the sheath so that the second locking element is adjacent the first locking element.

In the procedure e)-g) are preferably performed laparoscopically. Further, a)-h) may be practiced to repair an apical descent, and additionally, prior to g) and h), the procedure may include i) repairing a cystocele and/or rectocele vaginally using altered vaginal mesh components, e.g. having anterior or posterior arms.

The invention can also be practiced to perform laparoscopically assisted vaginal hysteropexy by attached a modified first mesh component to the cervix.

There are numerous advantages of the invention compared to conventional sacrocolpopexy. These advantages include:

Avoids having to create a space between vagina/bladder, vagina/rectum. This is a source of injury to the bladder and is a time consuming part of the procedure. When it is done vaginally, it is also easier.

Avoids the need for laparoscopic suturing. The lack of this difficult skill is a significant reason why this surgery is done by a select number of gynecologists/urologists. The inventive procedure avoids several steps where laparoscopy is historically required (suturing mesh to vagina, suturing mesh to sacrum, closing the peritoneal incision).

Avoids difficulty in tensioning the mesh. The mesh tension is assessed by looking in the vagina before the final anchor is placed in the sacrum. This is extremely difficult when using a robot (which is docked between the patient's legs and obstructs vaginal access).

Allows for easy repair of concurrent cystocele/rectocele, if applicable. This usually requires completing the entire abdominal cases and then transitioning to a vaginal surgery. Alternatively, some people try to get the Y-arms far enough down to fix these defects, thereby increasing the risk of bladder or rectal injury. According to the invention, one just extends the vaginal incision to expose and fix the other defects.

The invention is easily practiced using many existing off the shelf components (e.g. the bone screw, locking ring, and cystocele obturator fascia anchors). However, according to the invention, conventional components can easily be replaced with other technology. Or, one can avoid the need for a bone screw and locking ring (or any technology) by just suturing the mesh into the sacrum (still a lot less suturing than usually required).

Allows for development in combination with novel techniques. Gaining momentum is "single-port" laparoscopy. This is putting all of the instruments through one port, one incision. Usually, laparoscopic sacrocolpopexy requires at least five incisions. The less complicated the procedure, the more likely it can be done. Removing all the suturing through the use of the "passing" technique of the invention makes a single-port approach even more accessible.

It is the primary object of the invention to provide improved procedures and devices for repairing vaginal prolapse, and related conditions. This and other objects of the invention will become clear from the detailed description of the invention, and from the appended claims.

BRIEF DESCRIPTION OF THE DRAWINGS

All the drawing figures are schematic.

FIG. 16 shows the device of FIG. 10 in association with a spreader during practice of one aspect of the invention while

FIGS. 20, 22, and 24 are end views of components during the vaginal part of an exemplary procedure according to the invention, while

FIG. 27 is a side view illustrating the components of FIG. 26 after the locking elements are brought into operative association with each other, and tensioning of the second mesh component, while

FIG. 29 is a view like that of FIG. 28 only illustrating a modification of the invention after completion of laparoscopically assisted vaginal hysteropexy, while

DETAILED DESCRIPTION OF THE DRAWINGS

Figure 1:
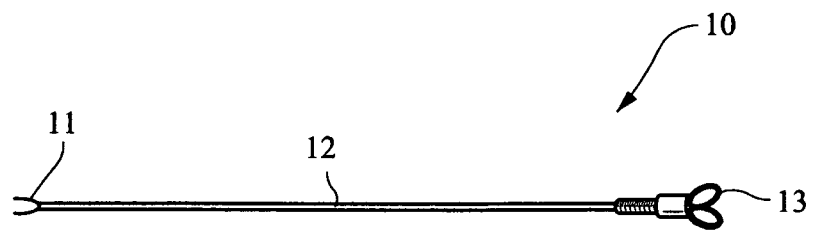
FIGS. 1 and 2 are side views of an exemplary device for effecting mobilization of the peritoneum according to the invention, FIG. 2 showing the device sheathed and with the handle removed.
Figure 2:
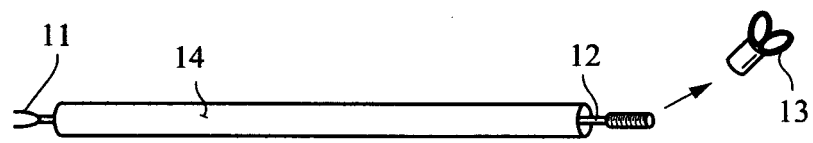

The drawings schematically illustrate some exemplary devices and procedures according to the invention. For example, FIG. 1 shows a device for effecting mobilization of the peritoneum according to the invention, in the form of an exemplary spreader 10 having jaws 11, a flexible shaft 12, and a removable handle 13. As seen in FIG. 2, when the handle 13 is removed, a sheath 14 of sterilized biocompatible material may be slipped over the shaft 12 and jaws 11, and the spreader 12 removed through the sheath 14 from a patient's body.

While the spreader 10 is desirable to effect mobilization, other devices can be utilized for that purpose. For example, mobilization of the peritoneum may be practiced using standard laparoscopic instruments, such as graspers and scissors.

Figures 3, 4:
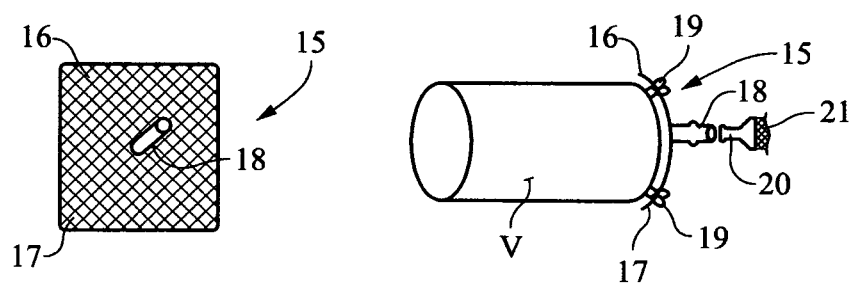
FIGS. 3 and 4 are end and side views, respectively, of an exemplary first mesh component of a surgical implantable article according to the invention, with a first locking element, FIG. 4 showing it in operative association with a vagina.

FIG. 3 shows one form of a first mesh component 15 of a surgical implantable article according to the invention comprising first and second mesh components. The first mesh component 15 comprises a generally rectangular component having anterior and posterior surfaces 16, 17 and a truncated stem including (and in the case of the device of FIG. 3 essentially defined by) a first locking element 18. As seen in FIG. 4, the surfaces 16, 17 are fixed—as by sutures 19—to the apex of a vagina V, with the first locking element 18 extending outwardly from the vagina V. FIG. 4 also shows the second locking element 20 of a second mesh component 21 of the surgical implantable article, as will be hereinafter described.

Figure 5:
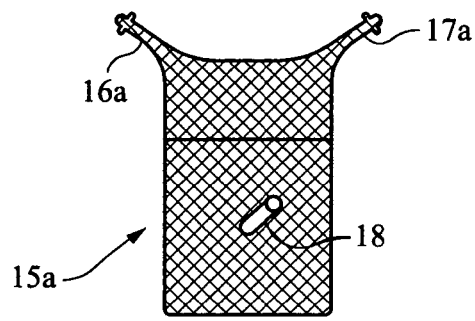
FIGS. 5 and 6 are end views of two modified forms of the first mesh component of FIG. 3.
Figure 6:
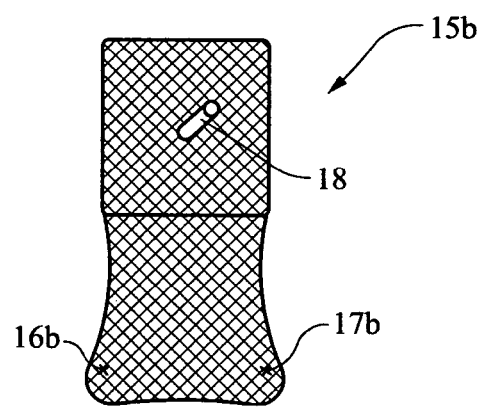

The first mesh component 15 may take a variety of other forms. FIGS. 5 & 6 show two other configurations the component may have. The component modification 15a in FIG. 5 comprises an anterior/apical mesh which has anterior arms 16a, 17a. The arms 16a, 17a may be anchored via standard suturing, trocar systems, or with other conventional devices. This embodiment is intended to be used to repair combined vaginal apex prolapse and a cystocele. The modification 15b in FIG. 6 comprises a posterior/apical mesh having arm portions 16b, 17b. This embodiment is intended to be used to repair combined vaginal prolapse and a rectocele. Other configurations are also possible.

Figure 7:
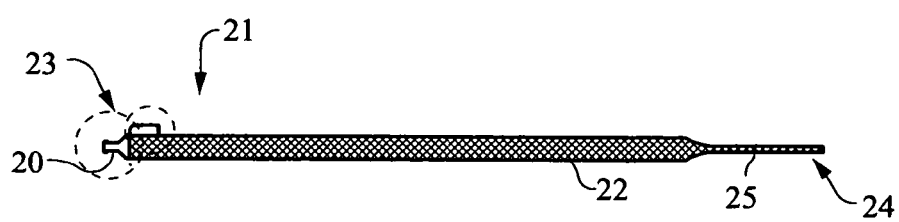
FIG. 7 is a side view of an exemplary second mesh component according to the invention, with second locking element.

FIG. 7 schematically illustrates in more detail than FIG. 4 an exemplary second mesh component 21 according to the invention, with second locking element 20. The component 21 comprises an elongated base 22 having distal 23 and proximate 24 ends, with the second locking element 20 operatively associated with the distal end 23. At the proximal end 24, the elongated base 22 illustrated in FIG. 7 has a thinned neck 25 that allows it to be drawn through a locking ring attached to the sacrum.

The mesh components 15, 21 preferably are made of the same material(s) (e.g. biocompatible polypropylene) as the surgical implantable article described in U.S. Pat. No. 6,592, 515.

Figure 8:
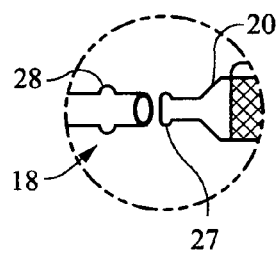
FIG. 8 is a side detail view of the first and second locking elements of FIGS. 3 and 7 moving into operative cooperative relationship with each other.

FIG. 8 schematically illustrates the locking elements 18, 20 according to the invention just before they are brought into operative, locking, association with each other. The details of how the locking elements 18, 20 cooperate to positively lock together are not important, only that they can be surgically moved together relatively easily in a patient's body and do become securely locked together so that they do not separate during subsequent patient activity. In the exemplary embodiment illustrated, the element 20 comprises a male locking element with an elastic annular portion 27 which is deformed radially when it enters the open end of the female locking element 18, but ultimately flexes outwardly when it engages the enlarged interior diameter annular portion 28 of the element 18, and is held in place in the portion 18 by the elastic nature of the element 27. Many alternative configurations may be used.

Figure 9:
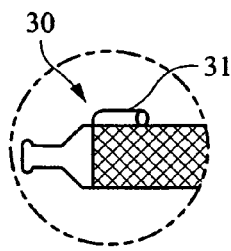
FIG. 9 shows a second mesh component as in FIG. 7 including an insertion site for a stylette.
Figure 10:
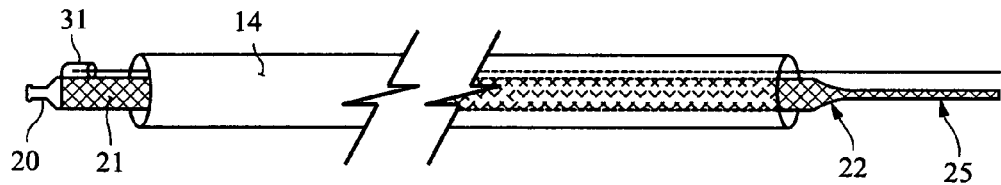
FIG. 10 is a primarily isometric view of a stylette being used to advance the second mesh component into a locking position.

FIG. 9 illustrates an insertion site 30 for a stylette 31 between the locking element 20 and the mesh base 21, and FIG. 10 shows the stylette 31 being used to advance the mesh base 21 through the sheath 14 to move the second locking element 20 into position adjacent the first locking element 18 (as in FIG. 8).

Figure 11:
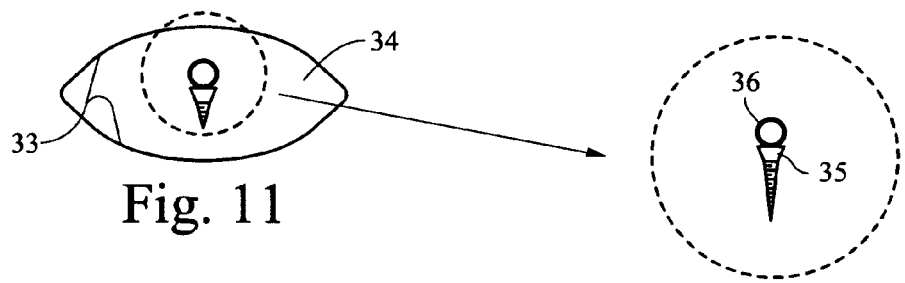
FIG. 11 is a lateral view of one way the second mesh component can be fixed to the sacrum according to the invention.
Figure 12:
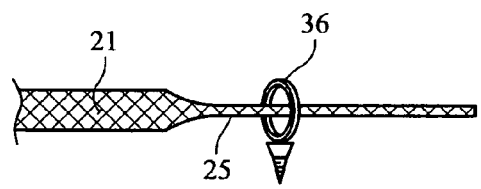
FIG. 12 is a side view of the proximate end section of the second mesh component.

FIG. 11 shows a lateral view of one way the proximate end 25 of the mesh base component 21 can be fixed to the sacrum. FIG. 11 shows a peritoneal incision 33 exposing the patient's sacrum promontory 34. A conventional straight-in bone screw 35 is screwed into the promontory 34, the screw 35 having a conventional locking ring 36 extending upwardly therefrom, the proximate end 25 passing through the ring 36. FIG. 12 is a side view showing the proximate end 25 passing through the ring 36, the mesh 21 tensioned the desired amount by pulling the end 25 through the ring 36. This anchoring procedure is merely exemplary—multiple other anchoring mechanisms may be used, including alternative locking devices.

Figure 13:
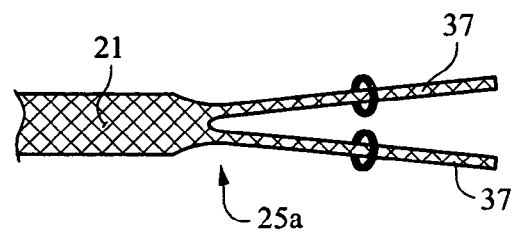
FIGS. 13 and 14 are side views of modified forms of the proximate end section of the second mesh component of FIG. 12.
Figure 14:
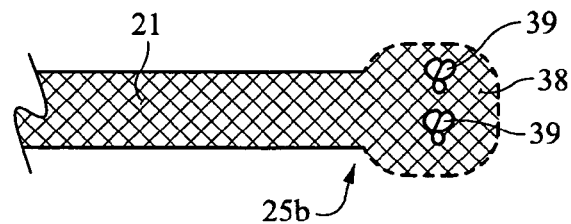

While FIGS. 7 & 11 show the proximate end 25 of mesh base 21 with a thinned neck, other configurations of the end 25 may be provided. For example, FIG. 13 schematically shows the end 25a with two spaced arms 37, each passing through a locking ring 36. FIG. 14 schematically shows the end 25b with a wider termination 38 to facilitate standard suture (see sutures 39) fixation of the mesh base 21 to the sacrum promontory 34. Other configurations are also possible.

Figure 15:
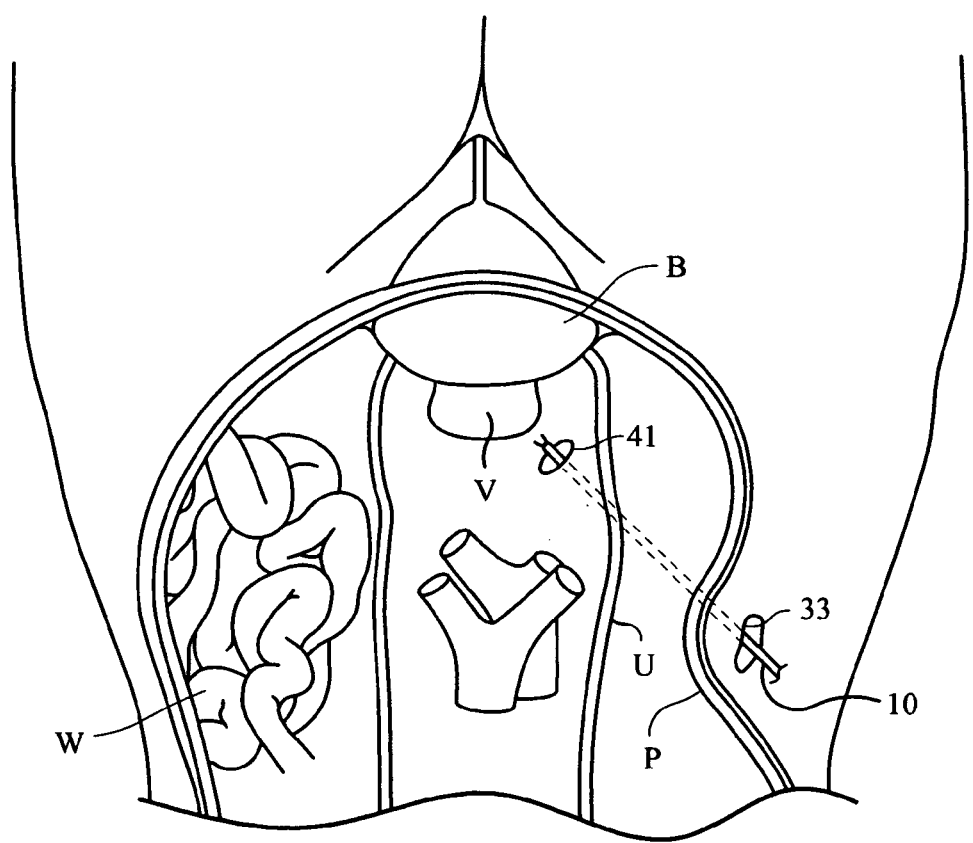
FIG. 15 illustrates a patient's pelvic area organs during exposure and mobilization according to the invention.

FIG. 15 schematically illustrates a female patient's pelvic area organs during exposure and mobilization according to an exemplary surgical procedure of the invention. The organs include the vagina V, bladder B, bowel W, and a ureter U, with the spreader 10 of FIG. 1 shown passing through a relatively small incision 33 in the peritoneum P like that in FIG. 9, and another small peritoneal incision 41 near the vagina V, to effect mobilization. The spreader 10 is preferably inserted laparoscopically.

Figure 16:
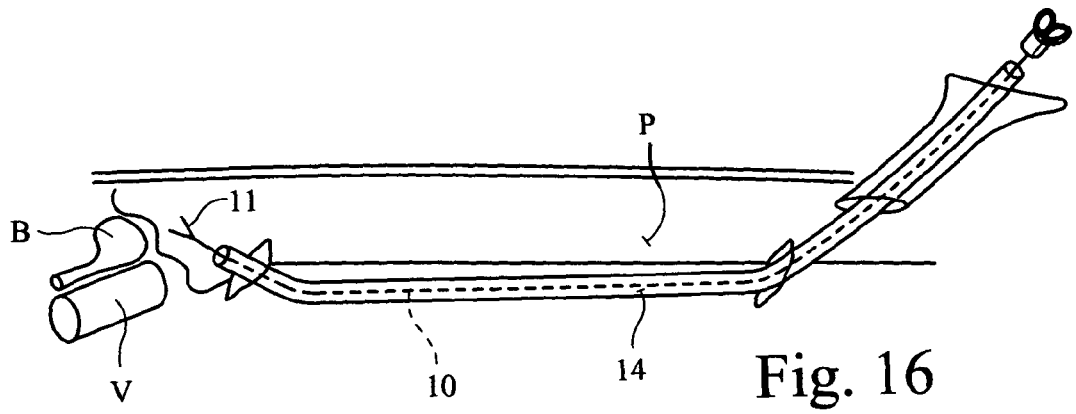
Figure 17:
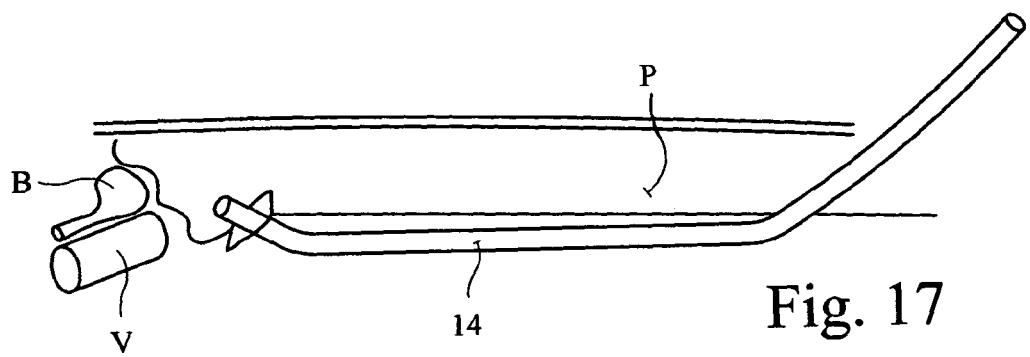
FIG. 17 is the same as FIG. 16 with the spreader removed.
Figure 18:
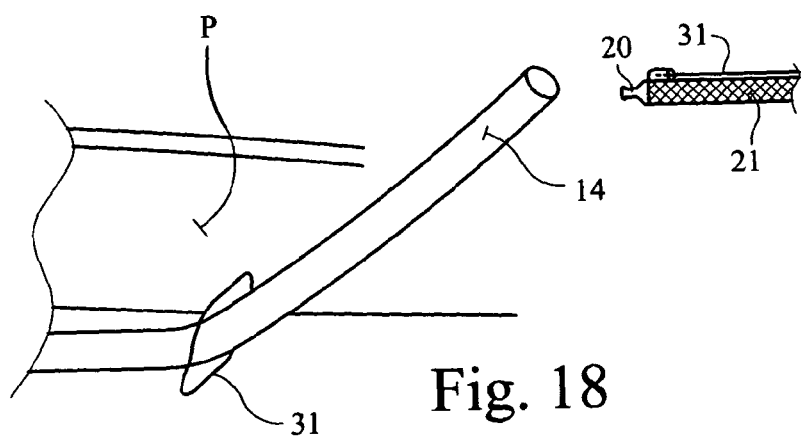
FIG. 18 is a side view showing the start of insertion of the second mesh component into the proximal open end of the sheath of FIGS. 16 & 17.
Figure 19:
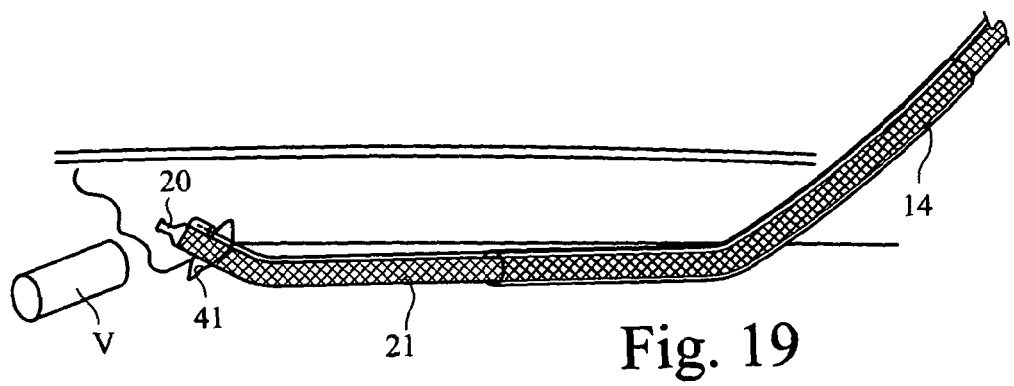
FIG. 19 is similar to FIG. 17 only showing the sheath partially removed.

FIG. 16 shows the sheath 14 advanced over the spreader 10, after the handle (13 in FIG. 1) is removed. A trocar is shown in this figure to illustrate the performance of this technique laparoscopically. The sheath 14 and spreader 10 are beneath the peritoneum P. FIG. 17 shows the spreader removed from the sheath 14, and FIG. 18 shows the start of the mesh body 21 being inserted into the proximal open end of the sheath 14, using the stylette 31. Once the locking element 20 is in proper position (FIG. 19) the sheath 14 is removed, the sheath 14 being shown partially removed in FIG. 19.

Figure 20:
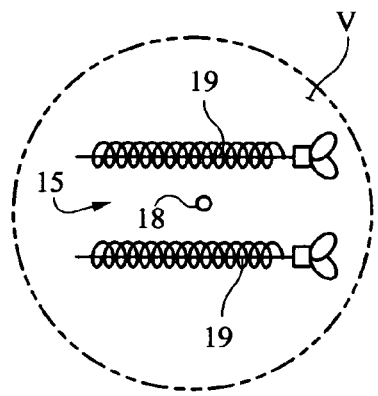
Figure 21:
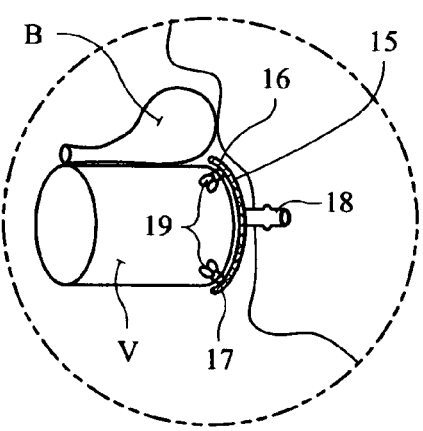
FIGS. 21, 23 and 25 are lateral views of the components of FIGS. 20, 22, and 24, respectively, in association with a vagina and bladder.
Figure 22:
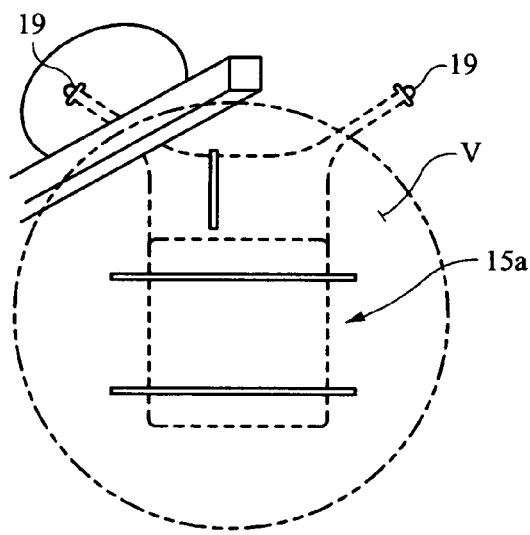
Figure 23:
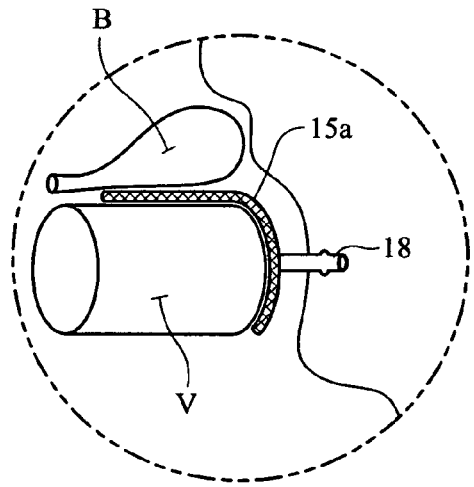
Figure 24:
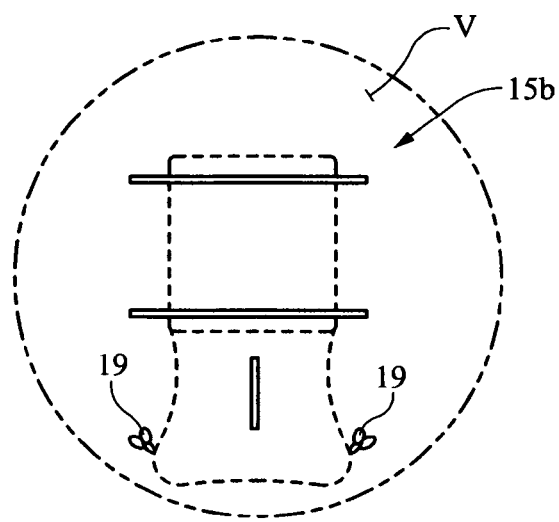
Figure 25:
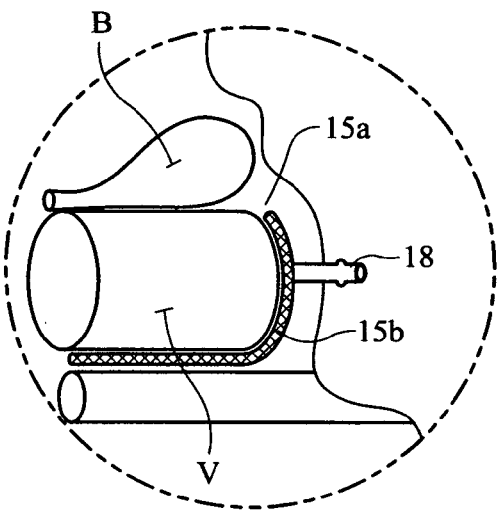

The vaginal part of the procedure according to the invention is illustrated schematically in FIGS. 20-25. FIGS. 21, 23 & 25 are lateral views of what is shown in FIGS. 20, 22 & 24, respectively. After the apical flap of the vagina V is raised, the first mesh component 15 is sutured into place, and with the first locking element 18 extending outwardly therefrom, as illustrated. The vaginal incisions are then closed (19 in FIG. 20). The only differences between FIGS. 20, 21 and 22, 23 and 24, 25 are the use of the particular configurations of the vaginal meshes 15, 15a, and 15b, respectively, from FIGS. 3, 5 and 6. FIGS. 22-25 illustrate alternate vaginal mesh designs to allow for both cystocele (FIGS. 22 & 23) and rectocele (FIGS. 24 & 25) repair in combination with vaginal apex prolapse.

While the invention has been described with respect to the first locking element 18 attached at all times to the mesh component 15, if desired the locking element 18 can initially be separate and attached thereto once the mesh component 15 (or 15a or 15b) has been sutured to the vagina V.

Figure 26:
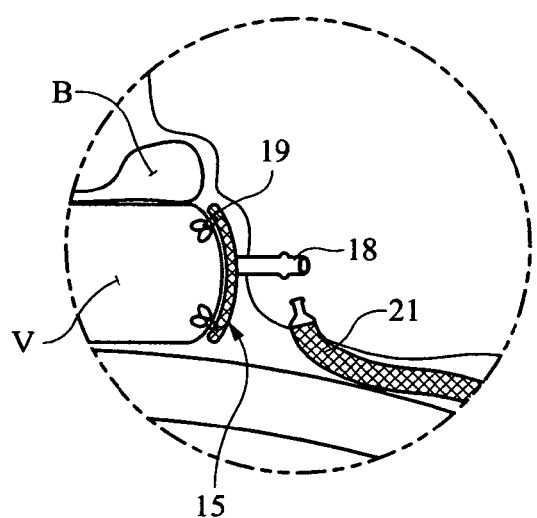
FIG. 26 is a primarily lateral view of components during the practice of an exemplary procedure according to the invention just before locking elements are brought into operative association with each other.
Figure 27:
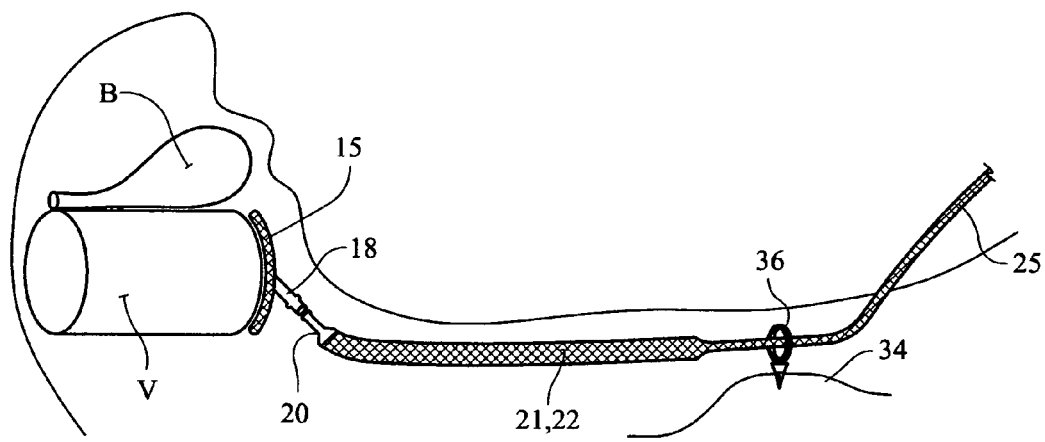
Figure 28:
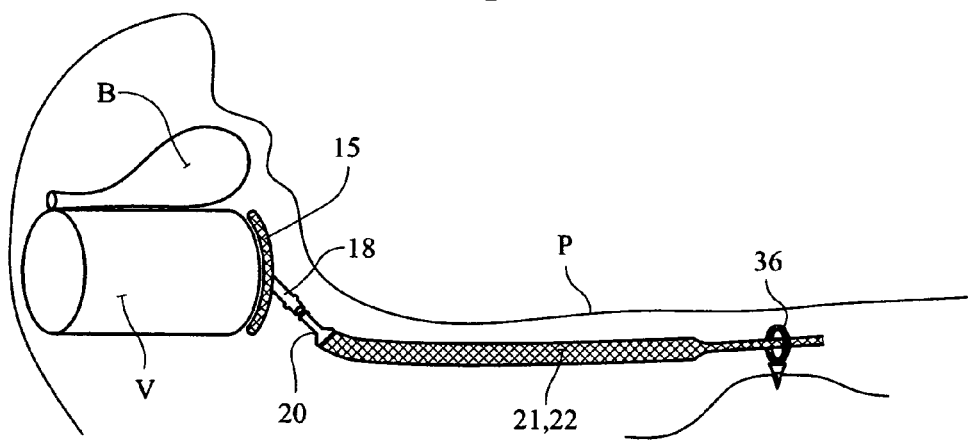
FIG. 28 is a view like that of FIG. 27 after completion of an exemplary surgical procedure according to the invention.

FIG. 26 shows the locking elements 18, 20 being brought together, which may be done laparoscopically. The elements 18, 20, when brought together, substantially permanently (e.g. for the life of the patient) hold the mesh components 15, 21 together. FIG. 27 shows tensioning of the base mesh 21 by pulling it through the locking ring 36 attached to the sacrum promontory 34 and fixing it in place, as is conventional per se. FIG. 28 schematically shows the components as positioned in the patient after completion of the surgical procedure, the peritoneal incision (33) having been closed in a conventional manner.

Figure 29:
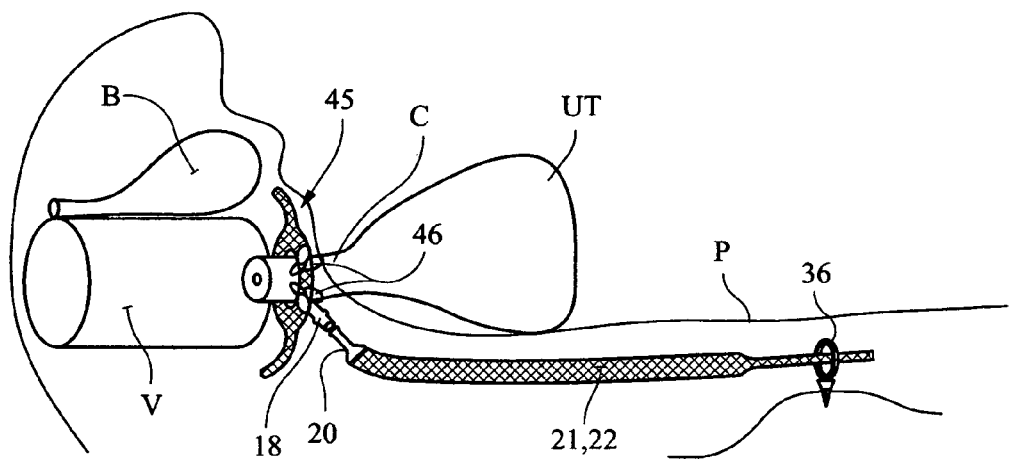
Figure 30:
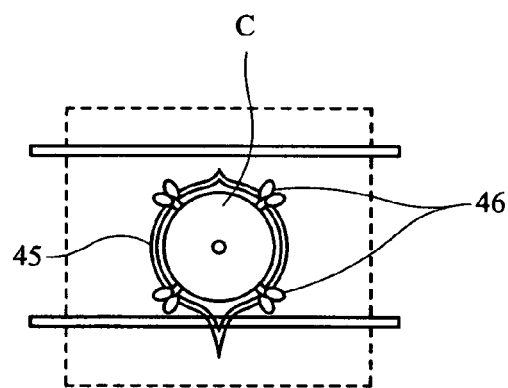
FIG. 30 is a detailed end view of the components of FIG. 29 showing the mesh component affixed to a cervix at four points.

FIGS. 29 and 30 show a modification of the invention for laparoscopically assisted vaginal hysteropexy. As seen in both figures, a mesh 45 according to the invention has a central aperture which receives the cervix C of a uterus UT. The mesh 45 is adapted to allow for a "bridge" around the cervix C, preferably with four point cervical fixation, such as provided by sutures 46. Only two sutures 46 are visible in FIG. 29, but all four are visible in FIG. 30.

Figure 31:
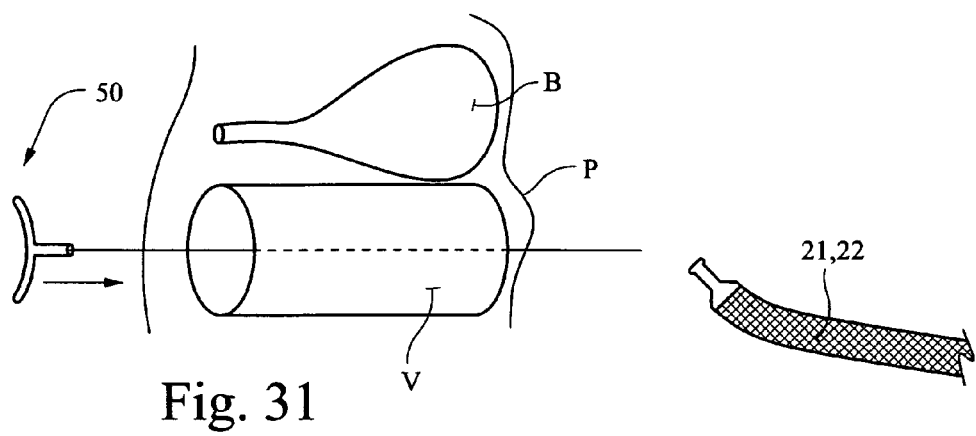
FIGS. 31-33 are consecutive side views of components according to the invention during a procedure for safe entry of the first mesh component into the peritoneum.
Figure 32:
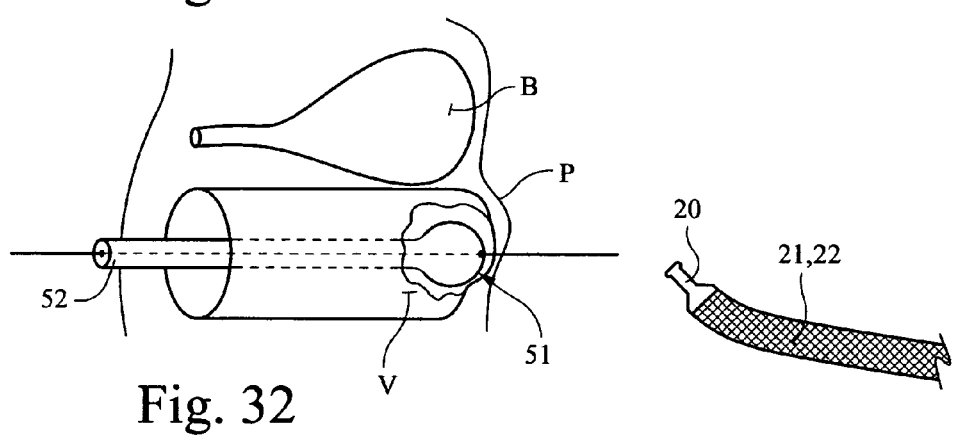
Figure 33:
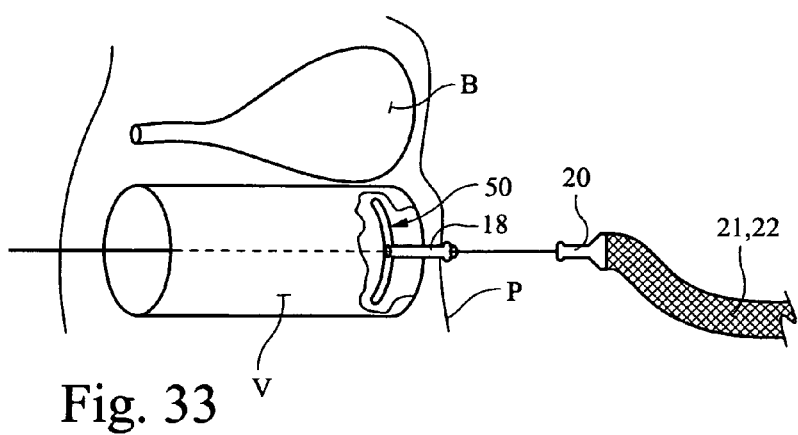

FIGS. 31-33 show modifications according to the invention for providing safe entry into the peritoneum. FIG. 31 shows a vaginal mesh 50 according to the invention which is designed to be advanced over a stylette (not shown in FIGS. 31-33, but to extend along the solid/dotted line passing through the vagina V and peritoneum P) under direct vision. The stylette is advanced through the vagina V and peritoneum P and the locking element of vaginal mesh 50 is ultimately brought into operative association with the locking element 20 of a mesh component 21 (see FIG. 33), as earlier described.

FIG. 32 shows a modified tubular vaginal sizer 52 having a bulbous free end 51 which is used to guide the stylette. The stylette passes through the hollow interior of the tubular sizer 52, and the bulbous end 51. Both the sizer 52, and especially the bulbous end 51 thereof, allow injury to the bladder B to be avoided, and also facilitate the ability to avoid bowel injury.

FIG. 33 shows the mesh 50 after it has been inserted over the stylette into the vagina V with the locking element 18 thereof passing through the peritoneum P and ready to be connected to the locking element 20 of the mesh 21.

While various embodiments of the invention have been illustrated and described, they are non-limiting; the invention is to be limited in scope only by the prior art, and according the broadest interpretation of the appended claims consistent with the prior art.

I claim:

1. A surgical procedure for repairing vaginal prolapse, including apical descent, cystocele and/or rectocele, in a patient having a vagina with a vaginal apex, and a sacrum, comprising: a) exposing a patient's peritoneum; b) making a peritoneal incision over the patient's sacrum; c) mobilizing the peritoneum; d) incising the patient's vagina and attaching anterior and posterior surfaces of a first biocompatible surgically implantable component, with a truncated stem and first locking element, to the apex of the patient's vagina; e) passing a biocompatible surgically implantable base component having a second locking element at a distal end, and a proximal end, underneath the peritoneum; f) moving the first and second locking elements together into locking relationship; g) anchoring the biocompatible surgically implantable base to the sacrum, so that the first and base components suspend the vaginal apex from the sacrum; and h) closing the peritoneal incision.

2. A procedure as recited in claim 1 wherein d) is performed vaginally using as the first component, a generally rectangular first component, and e) and g) are performed abdominally.

3. A procedure as recited in claim 1 wherein g) is performed using a conventional bone screw affixed to the sacrum and a conventional locking ring affixed to the bone screw, and the base component is tensioned using the locking ring and then fixed to the locking ring; wherein c) is performed by passing a spreader, having jaws connected to a flexible shaft, underneath the peritoneum, the spreader also having a removable handle, and e) is performed by removing the handle, passing a sheath over the spreader shaft and jaws to an approximate location of the first locking element, removing the spreader shaft and jaws through the sheath, and using a stylette, inserting the base component through the sheath so that the second locking element is adjacent the first locking element.

4. A procedure as recited in claim 1 wherein e)-g) are performed laparoscopically.

5. A procedure as recited in claim 1 wherein a)-h) are performed to repair an apical descent in the farm of vaginal vault or uterine descensus.

6. A procedure as recited in claim 5 further comprising, prior to g) and h), i) repairing a cystocele or a rectocele vaginally using as the first and base components vaginal mesh components capable of repairing a cystocele or a rectocele.

7. A procedure as recited in claim 6 wherein i) is performed using as each of the first and base components, a generally rectangular mesh component having anterior and/or posterior arms.

8. A procedure as recited in claim 1 further comprising performing laparoscopically assisted vaginal hysteropexy.

9. A procedure as recited in claim 8 wherein d) is performed utilizing as the first component a component including a central aperture through which the cervix is passed, and further comprising j) affixing the first component to the cervix.

10. A procedure as recited in claim 1 wherein b) and d) are performed in part using a tubular vaginal sizer with a bulbous end through which a stylette is passed so as to maximize the ability to avoid injury to the bladder and bowel.

11. A procedure as recited in claim 1 wherein the first locking element is not initially attached to the first component, and further comprising attaching the first locking element to the first component after d) and prior to f).

12. A procedure as recited in claim 1 wherein d), e), and g) are performed using as each of the first and base components, first and base biocompatible surgically implantable mesh components.

13. A procedure as recited in claim 1 wherein f) is performed by moving the male locking element, with an elastic annular portion, on one of the components into operative association with the female locking element, with an enlarged interior diameter annular portion capable of receiving the annular portion of the male locking element, on the other of the components, so that the elastic annular portion of the male locking element is received by the enlarged interior diameter annular portion of the female locking element.

14. A procedure as recited in claim 1 wherein a)-h) are performed to perform a vaginal vault and cystocele combination repair.

15. A procedure as recited in claim 14 wherein a)-h) are performed using as the first biocompatible surgically implantable component, an anterior/apical mesh having first and second anterior arms.

16. A procedure as recited in claim 15 wherein the first locking element is not initially attached to the first component, and further comprising attaching the first locking element to the first component after d) and prior to f).

* * * * *